United States Patent
He et al.

(10) Patent No.: US 9,147,564 B2
(45) Date of Patent: Sep. 29, 2015

(54) ELECTRODE STRUCTURE FOR ION DRIFT TUBE AND ION DRIFT TUBE INCLUDING THE STRUCTURE

(71) Applicant: NUCTECH COMPANY LIMITED, Beijing (CN)

(72) Inventors: Wen He, Beijing (CN); Guanxing Li, Beijing (CN); Yuntai Bao, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 14/365,610

(22) PCT Filed: Dec. 13, 2012

(86) PCT No.: PCT/CN2012/086514
§ 371 (c)(1),
(2) Date: Jun. 13, 2014

(87) PCT Pub. No.: WO2013/086992
PCT Pub. Date: Jun. 20, 2013

(65) Prior Publication Data
US 2014/0353494 A1   Dec. 4, 2014

(30) Foreign Application Priority Data

Dec. 16, 2011   (CN) .......................... 2011 1 0422560

(51) Int. Cl.
G21K 5/04 (2006.01)
H01J 49/02 (2006.01)
G01N 27/62 (2006.01)
H01J 49/26 (2006.01)

(52) U.S. Cl.
CPC .............. *H01J 49/02* (2013.01); *G01N 27/622* (2013.01); *H01J 49/26* (2013.01)

(58) Field of Classification Search
USPC ...................... 250/396 R, 397, 281, 282, 283
See application file for complete search history.

(56) References Cited

U.S. PATENT DOCUMENTS

| 2001/0032929 A1 | 10/2001 | Fuhrer et al. |
| 2008/0135777 A1* | 6/2008 | Yamashita et al. ............ 250/397 |
| 2010/0282957 A1* | 11/2010 | Wouters et al. ............ 250/252.1 |

FOREIGN PATENT DOCUMENTS

| CN | 202373552 U | 8/2012 |
| WO | WO2010136779 | 12/2010 |

OTHER PUBLICATIONS

PCT/CN2012/086514 International Search Report mailed Jun. 20, 2013, 3 pages.
European Patent Application No. 12857104.9; Extended European Search Report; dated Jul. 8, 2015; 6 pages.

* cited by examiner

*Primary Examiner* — Nicole Ippolito
(74) *Attorney, Agent, or Firm* — Baker & Hostetler LLP

(57) ABSTRACT

An electrode structure for an ion drift tube and an ion drift tube with the electrode structure are disclosed. The electrode structure comprises an annular electrode. The annular electrode has an inner edge bent towards one side such that a section of a central portion of the annular electrode has a swallowtail shape. With the ion drift detection instrument, ions in a drift state can travel along focusing electric lines of force, and since the high-voltage intervals between the electrodes are increased at a uniform acceleration, the generated electric field enables the ions to be in a uniformly accelerated drift state so that both the sensitivity and resolution of the mobility spectrum of the detection instrument can reach optimum.

9 Claims, 2 Drawing Sheets

ELECTRODE STRUCTURE FOR ION DRIFT TUBE AND ION DRIFT TUBE INCLUDING THE STRUCTURE

CROSS-REFERENCE TO RELATED APPLICATIONS

This application is the National Stage of International Application No. PCT/CN2012/086514, filed Dec. 13, 2012, which claims the benefit of Chinese Patent Application No. 201110422560.2, filed Dec. 16, 2011, the disclosures of which are incorporated herein by reference in their entireties.

BACKGROUND OF THE INVENTION

1. Field of the Invention

The present invention relates to a field of ion drift technology, and in particular to an electrode structure for an ion drift tube and an ion drift tube including the same.

2. Description of the Related Art

In the field of safety inspection, detection of hazardous articles such as drugs, explosives, chemical agents and industrial toxicants is an extremely important work. Therefore, many detection instruments for the above articles have been developed. Currently, the detection instruments using the ion drift technology are most common. Two indexes that are most crucial in the ion drift technology are sensitivity and resolution of a detector. It is a main object of design and fabrication of the ion drift tube to optimize the two indexes. The ion drift tube is a core part of an ion mobility spectrometer and is used to generate a uniform electric field so that ions having different mobilities are separated. As shown in FIG. 1, in a conventional ion drift tube, drift of ions is controlled by a uniform high-voltage electric field by thin sheet electrodes 1 having the same size spaced equidistantly by means of insulating parts 3. In the ion drift tube, the ions drift in the air under the normal pressure. The uniform electric field generated by the conventional structure shown in FIG. 1 is an approximate model and a non-ideal uniform electric field. In addition, the ions are simultaneously subjected to factors such as the high-voltage electric field and air resistance. Therefore, uniform equidistant high-voltages cannot well generate pre-acceleration, focusing, a maximal amount of drift of the ions and the like. As a result, it is difficult for sensitivity and resolution of a mobility spectrum obtained by the ion mobility spectrometer to reach optimum.

SUMMARY OF THE INVENTION a. Technical Problem to be Solved

The technical problem to be solved by the present invention is how to provide an ion drift tube so that sensitivity and resolution of a mobility spectrum of a detection instrument with the ion drift tube reach optimum.

b. Technical Solution

In order to solve the above technical problem, the present invention provides an electrode structure for an ion drift tube comprising: an annular electrode, wherein the annular electrode has an inner edge bent towards one side such that a section of a central portion of the annular electrode has a swallowtail shape.

In accordance with an aspect of the present invention, the inner edge of the annular electrode has a substantially tapered shape.

The present invention also provides an ion drift tube comprising the above electrode structures arranged at intervals. The inner edges of the annular electrodes of the electrode structures are bent in a same direction, and the same direction is an opposite direction to an ion drift direction.

In accordance with an aspect of the present invention, the electrode structures are arranged at decreasing intervals in the opposite direction to the ion drift direction.

In accordance with an aspect of the present invention, the decreasing intervals have a ratio of $1.07^{n-1} : \ldots : 1.07 : 1$, where n is a number of the electrode structures in the ion drift tube.

In accordance with an aspect of the present invention, the inner edge of the annular electrode has a substantially tapered shape.

In accordance with an aspect of the present invention, a cross sectional area of a space defined by the inner edge of the annular electrode increases gradually in an ion drift direction.

In accordance with an aspect of the present invention, the ion drift tube further comprises an insulation part disposed between the electrode structures.

In accordance with an aspect of the present invention, the electrode structure has recesses on both sides at an outer peripheral portion, and both ends of the insulation part are disposed in the recesses.

In accordance with a further aspect of the present invention, the present invention provides an ion drift tube, the ion drift tube comprises electrode structures arranged at intervals, and the electrode structures are arranged at decreasing intervals in an opposite direction to an ion drift direction.

In accordance with an aspect of the present invention, the decreasing intervals have a ratio of $1.07^{n-1} : \ldots : 1.07 : 1$, where n is a number of the electrode structures in the ion drift tube.

c. Advantageous Technical Effect

In the ion drift detection instrument with the electrode structure and the ion drift tube of the present invention, ions in a drift state can travel along focusing electric lines of force, and since the high-voltage intervals between the electrodes are increased at a uniform acceleration, the generated electric field enables the ions to be in a uniformly accelerated drift state so that both the sensitivity and resolution of the mobility spectrum of the detection instrument can reach optimum.

DETAILED DESCRIPTION OF THE EMBODIMENTS

An electrode structure for an ion drift tube and an ion drift tube including the electrode structure according to the present invention are described in detail as below with reference to embodiments of the present invention taken in conjunction with the accompanying drawings.

Figure 2:
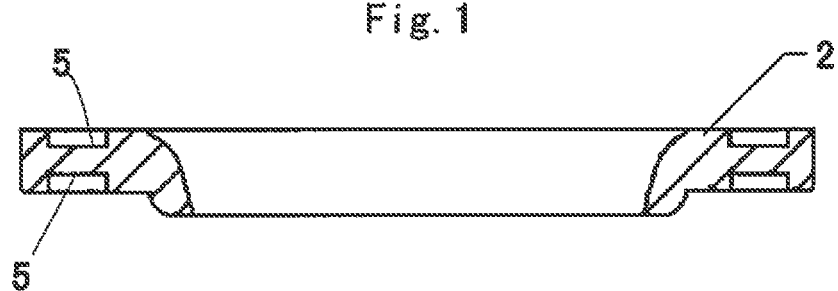
FIG. 2 is a schematic view showing an electrode structure for an ion drift tube according to an embodiment of the present invention.
Figure 3:
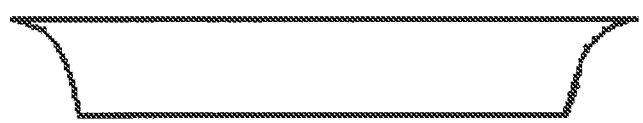
FIG. 3 is a schematic view showing a section of a central portion of the electrode structure for an ion drift tube according to an embodiment of the present invention.

As shown in FIG. 2, an electrode structure for an ion drift tube according to an embodiment of the present invention comprises an annular electrode. The annular electrode is hollow in a central portion and has an inner edge bent towards one side such that a section of the central portion of the annular electrode has a swallowtail shape as shown in FIG. 3. With such an arrangement in which an opening on one side of the annular electrode is contracted and an opening on the other side of the annular electrode is enlarged, the electric field applied to ions has a focusing function so as to force the ions in a drift state to travel along focusing electric lines of force.

Figure 1:
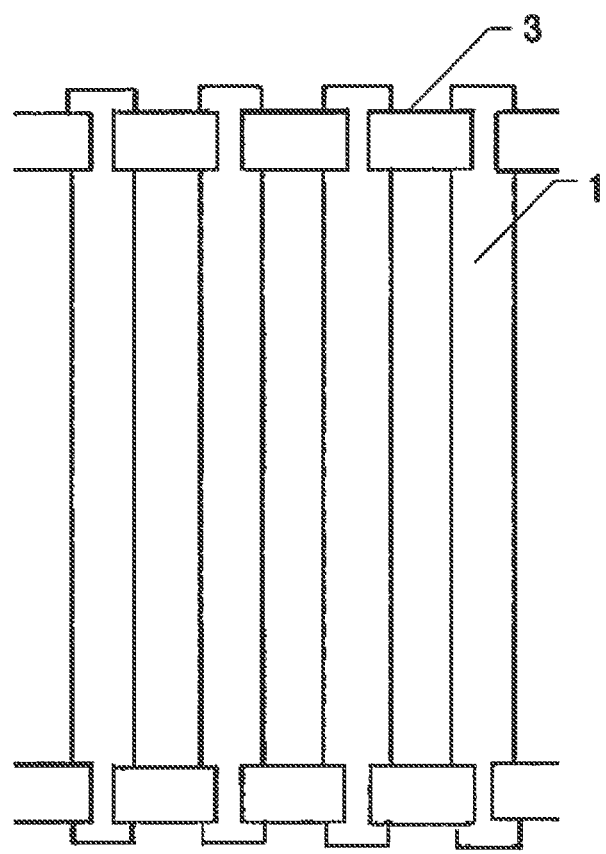
FIG. 1 is a schematic view showing a structure of a conventional ion drift tube.

As shown in FIGS. 1-2, the electrode structure is formed with recesses 5 on opposite sides at an outer peripheral portion, and opposite ends of the insulation part 3 are disposed in the recesses 5.

Figure 4:
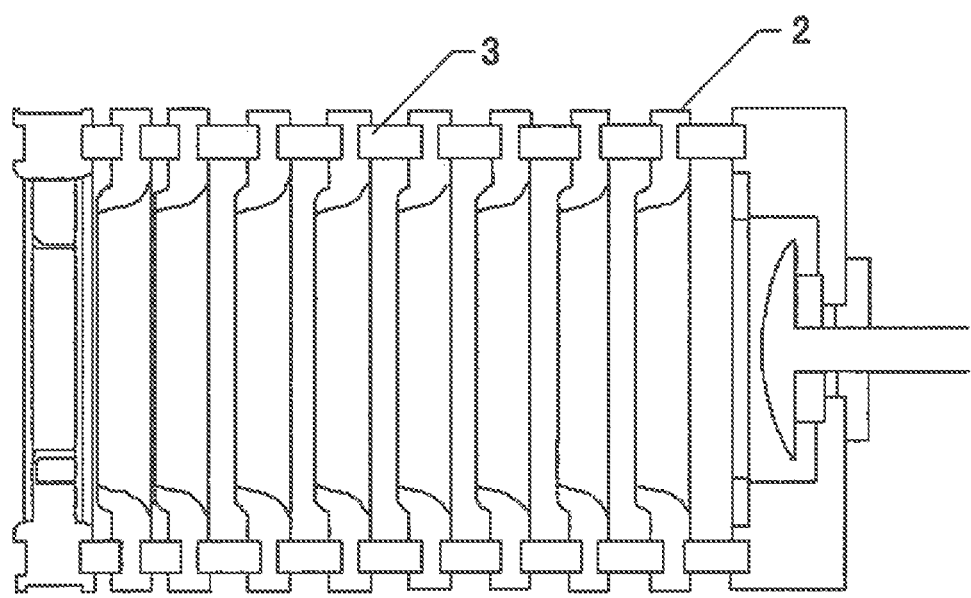
FIG. 4 is a schematic view showing a structure of an ion drift tube according to an embodiment of the present invention.

As shown in FIG. 4, an ion drift tube according to an embodiment of the present invention comprises the electrode structures 2 arranged at intervals as shown in FIG. 2, and the insulation parts 3 mounted between the electrode structures 2. The inner edges of the annular electrodes of the electrode structures are bent in a same direction, i.e., bent in an opposite direction to an ion drift direction, and generally bent towards a Faraday plate in the ion drift detection instrument. The electrode structures are also arranged at decreasing intervals in a direction toward the Faraday plate. The decreasing intervals have a ratio of $1.07^{n-1}: \ldots :1.07:1$, where n is a number of the electrode structures in the ion drift tube. The conventional intervals have a ratio of $1:1: \ldots :1$. The intervals are changed from the conventional intervals to the decreasing intervals. The high-voltage intervals between the electrodes enables the ions in a chamber of the ion drift tube to drift in a uniformly accelerated state, and in cooperation with the electrode structures having the focusing function, enable the sensitivity and resolution of the mobility spectrum to reach optimum when the ions finally arrive at the Faraday plate.

The above embodiments are only used to explain the present invention, and should not be construed to limit the present invention. It will be understood by those skilled in the art that various changes and modifications may be made therein without departing from the spirit of the present invention, the scope of which is defined in the appended claims and their equivalents.

The invention claimed is:

1. An electrode structure for an ion drift tube, comprising: an annular electrode, wherein the annular electrode has an annular inner edge bent towards one side in an axial direction of the annular electrode such that a section of a central portion of the annular electrode has a swallowtail shape.

2. The electrode structure of claim 1, wherein the annular inner edge of the annular electrode has a substantially tapered shape.

3. An ion drift tube, comprising a plurality of electrode structures arranged at intervals, wherein each of a plurality of electrode structures comprises an annular electrode which has an annular inner edge bent towards one side in an axial direction of the annular electrode such that a section of a central portion of the annular electrode has a swallowtail shape, the annular inner edges of the annular electrodes of the a plurality of the electrode structures are bent in a same direction, and the same direction is opposite to an ion drift direction.

4. The ion drift tube of claim 3, wherein the a plurality of electrode structures are arranged at decreasing intervals in a direction opposite to the ion drift direction.

5. The ion drift tube of claim 4, wherein the decreasing intervals have a ratio of $1.07^{n-1}: \ldots :1.07:1$, where n is a number of the a plurality of electrode structures in the ion drift tube.

6. The ion drift tube of claim 3, wherein the annular inner edge of the annular electrode has a substantially tapered shape.

7. The ion drift tube of claim 3, wherein a cross sectional area of a space defined by the annular inner edge of the annular electrode increases gradually in an ion drift direction.

8. The ion drift tube of claim 3, further comprising an insulation part disposed between each of the a plurality of electrode structures.

9. The ion drift tube of claim 8, wherein each of the a plurality of electrode structures has recesses on opposite sides at an outer peripheral portion, and opposite ends of the insulation part are disposed in the recesses.

* * * * *